US010493269B2

(12) United States Patent
Stoffregen et al.

(10) Patent No.: US 10,493,269 B2
(45) Date of Patent: Dec. 3, 2019

(54) LEADS FOR ELECTROSTIMULATION OF PERIPHERAL NERVES AND OTHER TARGETS

(71) Applicant: Boston Scientific Neuromodulation Corporation, Valencia, CA (US)

(72) Inventors: William Conrad Stoffregen, Lake Elmo, MN (US); Michael X. Govea, Glendale, CA (US); Bryan Allen Clark, Forest Lake, MN (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 249 days.

(21) Appl. No.: 15/608,573

(22) Filed: May 30, 2017

(65) Prior Publication Data
US 2017/0348522 A1 Dec. 7, 2017

Related U.S. Application Data

(60) Provisional application No. 62/344,839, filed on Jun. 2, 2016.

(51) Int. Cl.
*A61N 1/05* (2006.01)
*A61N 1/36* (2006.01)

(52) U.S. Cl.
CPC .......... *A61N 1/0553* (2013.01); *A61N 1/0529* (2013.01); *A61N 1/36017* (2013.01); *A61N 1/36* (2013.01); *A61N 1/3606* (2013.01)

(58) Field of Classification Search
CPC .. A61N 1/0553; A61N 1/0529; A61N 1/0534; A61N 1/0558; A61N 1/36017;
(Continued)

(56) References Cited

U.S. PATENT DOCUMENTS 3,769,984 A 11/1973 Muench
3,941,136 A  3/1976 Bucalo
(Continued)

FOREIGN PATENT DOCUMENTS

WO 98/37926 9/1998
WO 98/43700 10/1998
(Continued)

OTHER PUBLICATIONS

Rattay, F., "Analysis of Models for External Stimulation of Axons," IEEE Transactions on Biomedical Engineering, BME-33(10): 974-977, 1986.
(Continued)

*Primary Examiner* — Lindsey G Wehrheim
(74) *Attorney, Agent, or Firm* — Lowe Graham Jones PLLC; Bruce E. Black

(57) ABSTRACT

An electrical stimulation lead includes at least one lead body having a distal end portion, a proximal end portion, and a longitudinal length. The lead further includes a paddle body extending from the distal end portion of the at least one lead body, electrodes disposed along the paddle body, terminals disposed along the proximal end portion of the at least one lead body, and conductors electrically coupling the terminals to the electrodes. The lead further includes an anchoring device threadably disposed in at least a portion of the paddle body. The anchoring device has a head element and a tissue-engagement element fixed to the head element such that actuation of the head element urges the tissue-engagement element away from or toward the paddle body.

20 Claims, 13 Drawing Sheets

(58) Field of Classification Search
CPC .... A61N 1/36071; A61N 1/3787; A61N 1/36; A61N 1/3606
See application file for complete search history.

(56) References Cited

U.S. PATENT DOCUMENTS

| | | | |
|---|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,573,481 A * | 3/1986 | Bullara ............ A61N 1/0556 607/118 |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,433,735 A | 7/1995 | Zanakis et al. |
| 5,439,938 A | 8/1995 | Snyder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,876,399 A | 3/1999 | Chia et al. |
| 5,919,220 A | 7/1999 | Stieglitz et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Fielding et al. |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,594,805 B2 | 11/2013 | Hincapie Ordonez et al. |
| 8,612,025 B2 | 12/2013 | Neisz et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 2003/0040785 A1 | 2/2003 | Maschino et al. |
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |
| 2003/0236558 A1 | 12/2003 | Whitehurst et al. |
| 2004/0010303 A1 | 1/2004 | Bolea et al. |
| 2004/0034401 A1 | 2/2004 | Dahlberg et al. |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0173522 A1* | 8/2006 | Osorio ............. A61B 5/6864 607/116 |
| 2006/0184204 A1 | 8/2006 | He |
| 2006/0212075 A1 | 9/2006 | Marnfeldt |
| 2006/0241737 A1 | 10/2006 | Tockman et al. |

(56) References Cited

U.S. PATENT DOCUMENTS

| | | |
|---|---|---|
| 2006/0282145 A1 | 12/2006 | Caparso et al. |
| 2007/0150036 A1 | 6/2007 | Anderson |
| 2007/0219595 A1 | 9/2007 | He |
| 2008/0046055 A1 | 2/2008 | Durand et al. |
| 2008/0071320 A1 | 3/2008 | Brase |
| 2009/0187222 A1 | 7/2009 | Barker |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2010/0076535 A1 | 3/2010 | Pianca et al. |
| 2010/0241207 A1 | 9/2010 | Bluger |
| 2010/0268298 A1 | 10/2010 | Moffitt et al. |
| 2010/0298916 A1 | 11/2010 | Rabischong et al. |
| 2011/0004267 A1 | 1/2011 | Meadows et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0023974 A1 | 1/2013 | Amrani |
| 2013/0105071 A1 | 5/2013 | Digiore et al. |
| 2013/0172973 A1 | 7/2013 | Tockman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317587 A1 | 11/2013 | Barker |
| 2013/0325091 A1 | 12/2013 | Pianca et al. |
| 2014/0039587 A1 | 2/2014 | Romero |
| 2014/0074213 A1 | 3/2014 | Neisz et al. |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0202433 A1 | 7/2015 | Franke et al. |
| 2015/0202446 A1 | 7/2015 | Franke et al. |
| 2015/0366467 A1 | 12/2015 | De Kock et al. |
| 2017/0224982 A1 | 8/2017 | Nageri et al. |

FOREIGN PATENT DOCUMENTS

| | | |
|---|---|---|
| WO | 98/43701 | 10/1998 |
| WO | 2008019483 | 2/2008 |
| WO | 2008048471 | 4/2008 |
| WO | 2013188871 | 12/2013 |

OTHER PUBLICATIONS

U.S. Appl. No. 15/601,838, filed May 22, 2017.
U.S. Appl. No. 15/436,544, filed Feb. 17, 2017.
U.S. Appl. No. 62/429,650, filed Dec. 2, 2016.
U.S. Appl. No. 15/656,734, filed Jul. 21, 2017.
Rozman et al., "Selective Stimulation of Autonomic Nerves and Recording of Electroneurograms in a Canine Model," Artificiai Organs, 21(8): 592-595. 2008.
Polasek et al., "Stimulation Stability and Selectivity of Chronically Implanted Multicontact Nerve Cuff Electrodes in the Human Upper Extremity," IEEE Transactions on Neural Systems and Rehabilitation Engineering. vol. 17, No. 5, 428-437, Oct. 2009.
Plachta et al., "Blood pressure control with selective vagal nerve stimulation and minimal side effects," J. Neural Eng. 11 (2014) 036011 (15pp), 2014.

\* cited by examiner

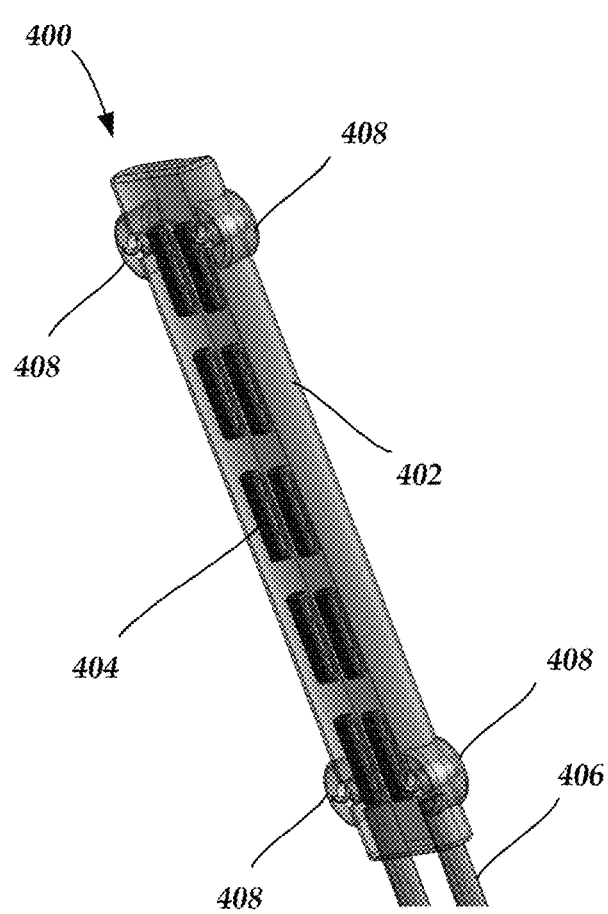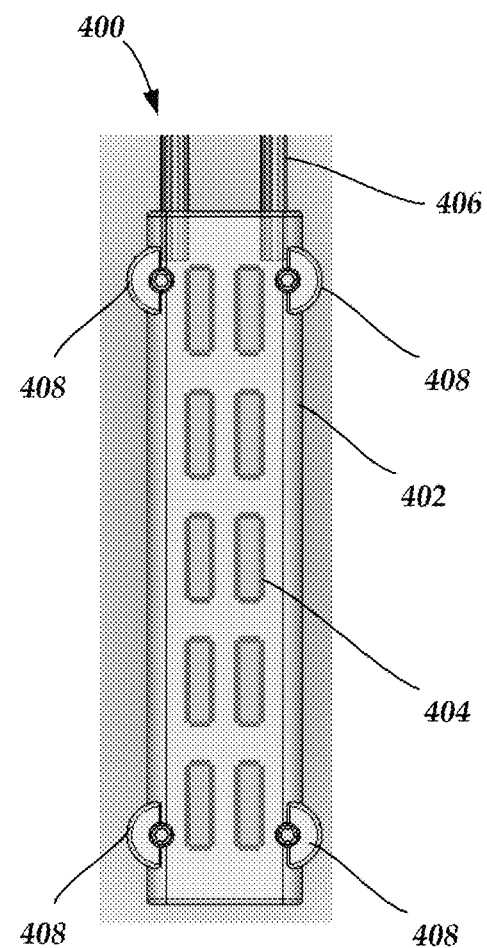
Fig. 4A  Fig. 4B
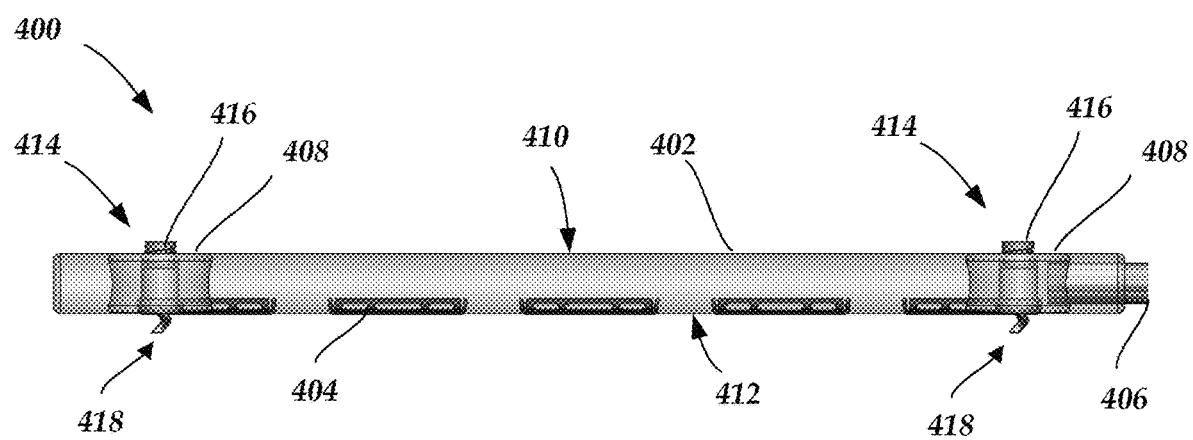
Fig. 4C

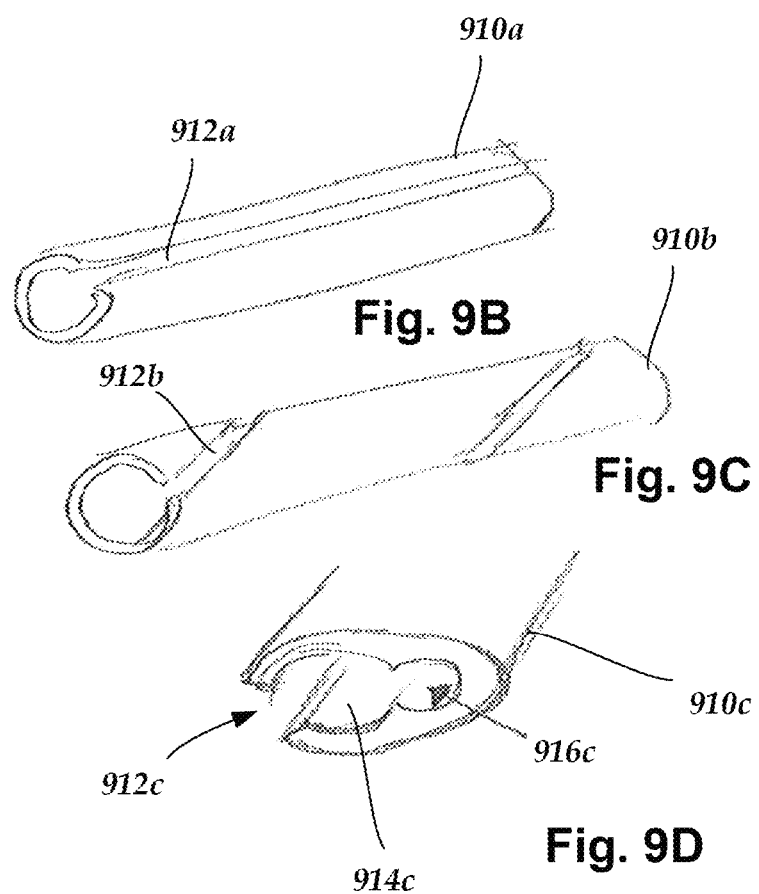

LEADS FOR ELECTROSTIMULATION OF PERIPHERAL NERVES AND OTHER TARGETS

CROSS-REFERENCE TO RELATED APPLICATIONS

This application claims the benefit under 35 U.S.C. § 119(e) of U.S. Provisional Patent Application Ser. No. 62/344,839, filed Jun. 2, 2016, which is incorporated herein by reference.

FIELD

The present invention is directed to the area of implantable electrical stimulation systems and methods of making, using and implanting the same. More specifically, the present invention is directed to systems and methods for leads that provide electrostimulation to peripheral nerves and other target tissues, as well as methods of making, using and implanting the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead that includes at least one lead body having a distal end portion, a proximal end portion, and a longitudinal length. The lead further includes a paddle body extending from the distal end portion of the at least one lead body, electrodes disposed along the paddle body, terminals disposed along the proximal end portion of the at least one lead body, and conductors electrically coupling the terminals to the electrodes. The lead further includes an anchoring device threadably disposed in at least a portion of the paddle body. The anchoring device has a head element and a tissue-engagement element fixed to the head element such that actuation of the head element urges the tissue-engagement element away from or toward the paddle body.

In at least some embodiments, the paddle body includes a protuberance extending from a remainder of the paddle body and at least a portion of the anchoring device is disposed in the protuberance. In at least some embodiments, the head element includes a recessed region configured to be engaged by a tool. The recessed region can be hexagonally.

In at least some embodiments, the lead includes at least one additional anchoring device threadably disposed in a different portion of the paddle body.

In at least some embodiments, the tissue-engagement element is a helical member. The anchoring device is disposed along a side portion of the paddle body, the anchoring device is disposed along an end portion of the paddle body, or some combination thereof.

In at least some embodiments, the paddle body includes a curved section located between the anchoring device and at least one additional anchoring devices. The curved section is configured for placement over a target tissue.

Another embodiment is an electrical stimulation lead for stimulating a target tissue that includes a lead body having a distal end portion, a proximal end portion, and a longitudinal length, electrodes disposed along the distal end portion of the lead body, terminals disposed along the proximal end portion of the lead body, and conductors electrically coupling the terminals to the electrodes. The distal end of the lead body includes a helical shape that variably locates the electrodes around the target tissue in both a longitudinal and circumferential direction.

In at least some embodiments, the lead includes a stylet extending through at least the distal end of the lead body. The stylet can be helically shaped nitinol wire.

In at least some embodiments, the distal end of the lead body is molded into the helical shape.

In at least some embodiments, the lead includes a sheath located over at least a section of the distal end portion of the lead body. And, the sheath may include a slit for sliding the sheath over the lead body and the target tissue.

A further embodiment is a method of implanting an electrical stimulation lead that includes the steps of (1) moving a distal end portion of the lead described above to be within a vicinity of a target tissue; (2) from a proximal end portion of the lead, inserting a stylet longitudinally into the lead, where a distal end portion of the stylet includes a helical shape; and (3) manipulating the stylet to urge the distal end portion of the lead to helically wrap around the target tissue. Inserting the stylet may include inserting a nitinol guidewire.

Yet another embodiment is an electrical stimulation lead that includes at least one lead body having a distal end portion, a proximal end portion, and a longitudinal length, a paddle body extending from the distal end portion of the at least one lead body, electrodes disposed along the paddle body, terminals disposed along the proximal end portion of the at least one lead body, and conductors electrically coupling the terminals to the electrodes. The lead further includes an anchoring element manipulatable to extend through at least a portion of the paddle body. The anchoring element has a distal end portion adaptable to become a tissue-engaging element when the distal end portion is urged out of the paddle body.

A further embodiment is an electrical stimulation system that includes any of the leads described above and a control module coupleable to the lead. The control module includes a housing and an electronic subassembly disposed in the housing. The lead further includes a connector for receiving the electrical stimulation lead, the connector having a proximal end, a distal end, and a longitudinal length. The connector includes a connector housing defining a port at the distal end portion of the connector. The port is configured and arranged for receiving the proximal end portion of the lead body of the electrical stimulation lead. The connecter further includes connector contacts disposed in the connector housing. The connector contacts are configured and arranged to couple to at least one of the terminals disposed on the proximal end portion of the lead body of the lead. In at least some embodiments, the lead includes a lead extension coupleable to both the lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic, perspective view of a paddle-style lead having a plurality of anchoring devices according to an embodiment of the present invention;

FIG. 4B is a plan view of the paddle-style lead of FIG. 4A;

FIG. 4C is a side elevational view of the paddle-style lead of FIG. 4A;

FIG. 9B is a schematic, perspective view of a sheath for the helical lead of FIG. 9A according to an embodiment of the present invention;

FIG. 9C is a schematic, perspective view of another sheath for the helical lead of FIG. 9A according to another embodiment of the present invention;

FIG. 9D is a schematic, perspective view of yet another sheath for the helical lead of FIG. 9A according to yet another embodiment of the present invention.

DETAILED DESCRIPTION

The present invention is directed to the area of implantable electrical stimulation systems and methods of making, using and implanting the same. More specifically, the present invention is directed to systems and methods for leads that provide electrostimulation to targets such as peripheral nerves, as well as methods of making, using and implanting the leads and electrical stimulation systems.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties. Examples of implanting or anchoring leads may be found in U.S. Pat. Nos. 8,019,443; 8,718,790; 8,768,488; 8,849,422; and U.S. Patent Publication Nos. 2012/0185027; 2013/01317518, which are incorporated by reference in their entireties.

Figure 1:
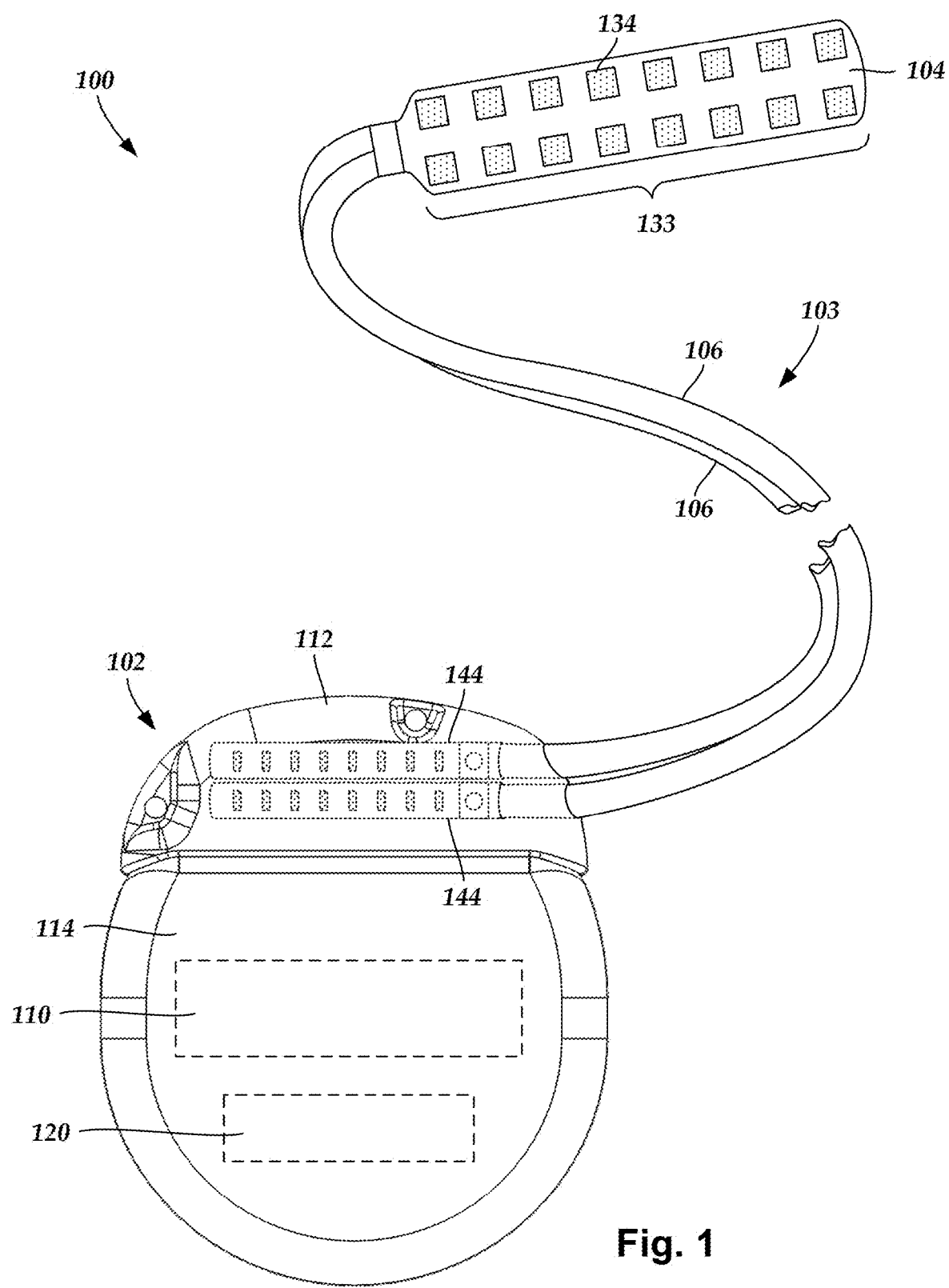
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
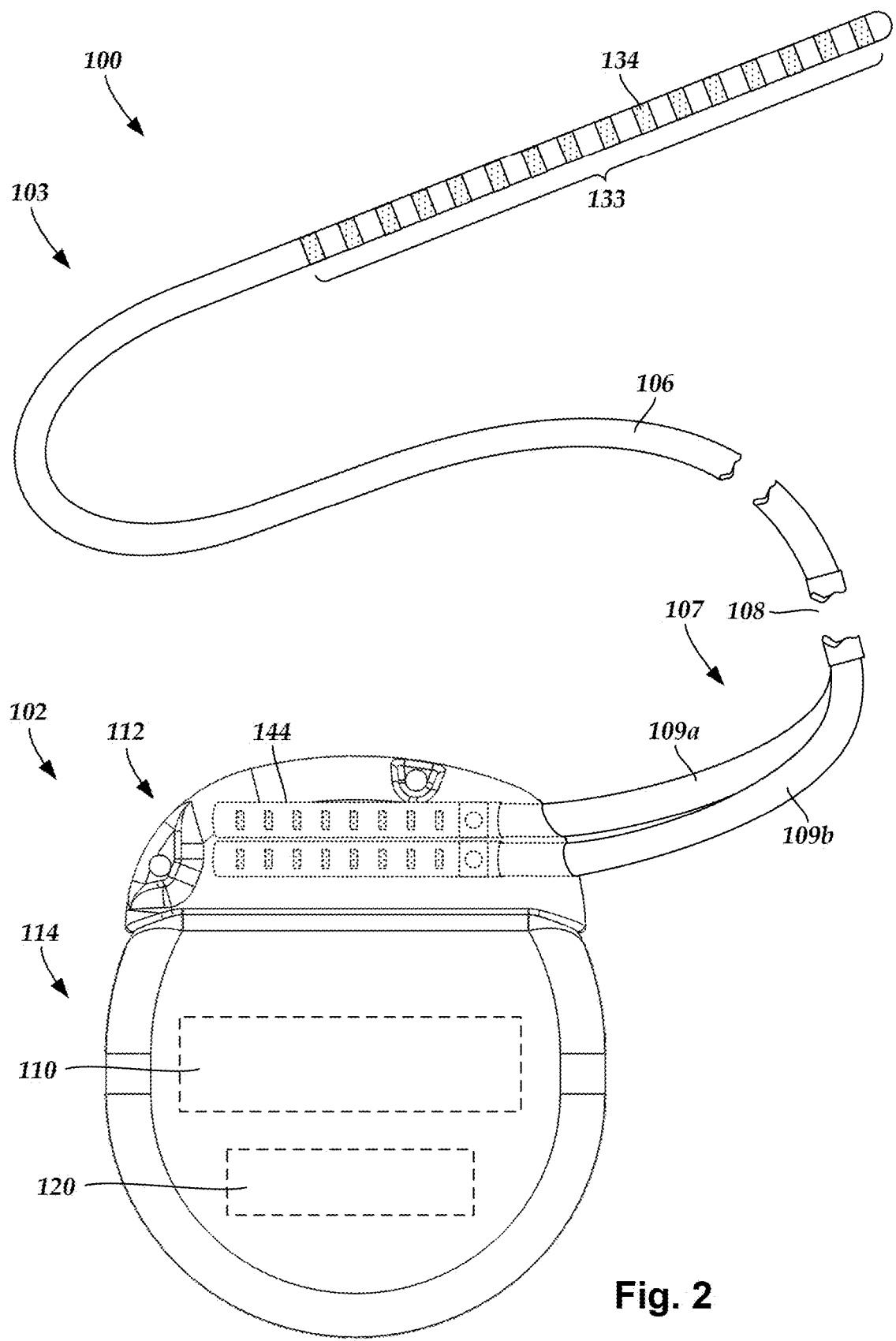
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
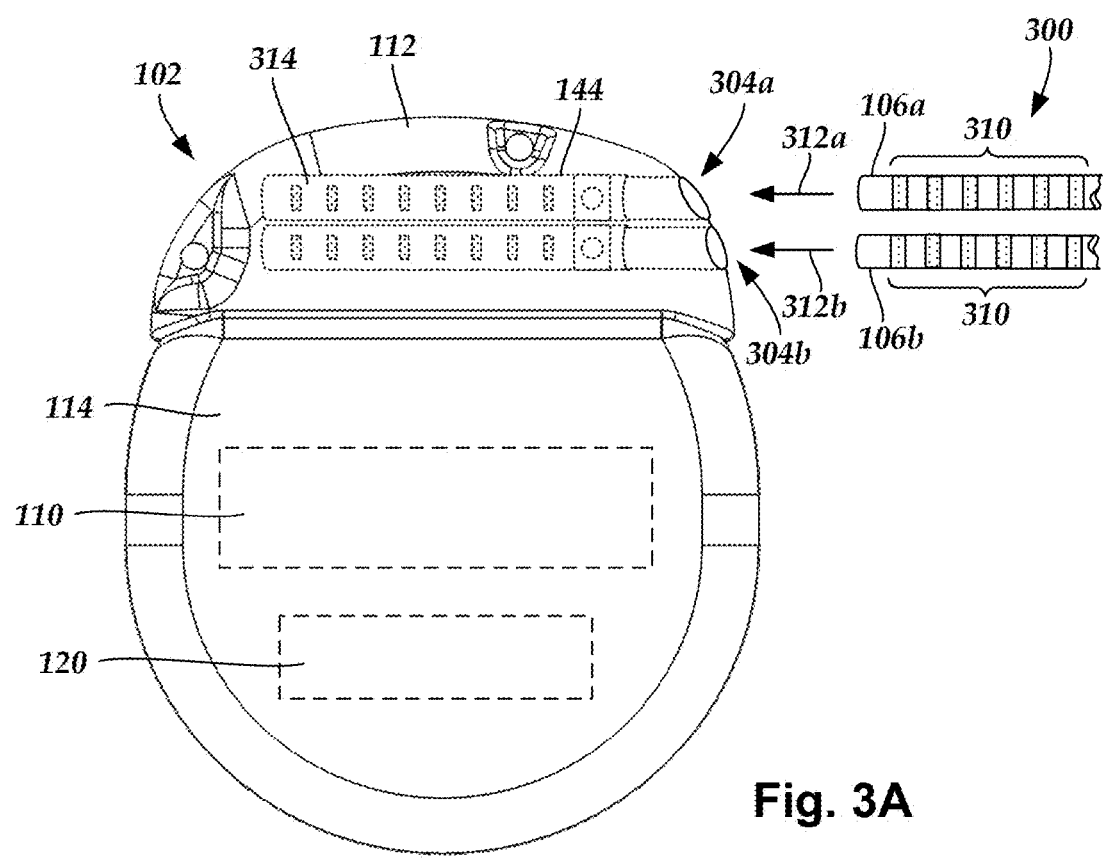
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
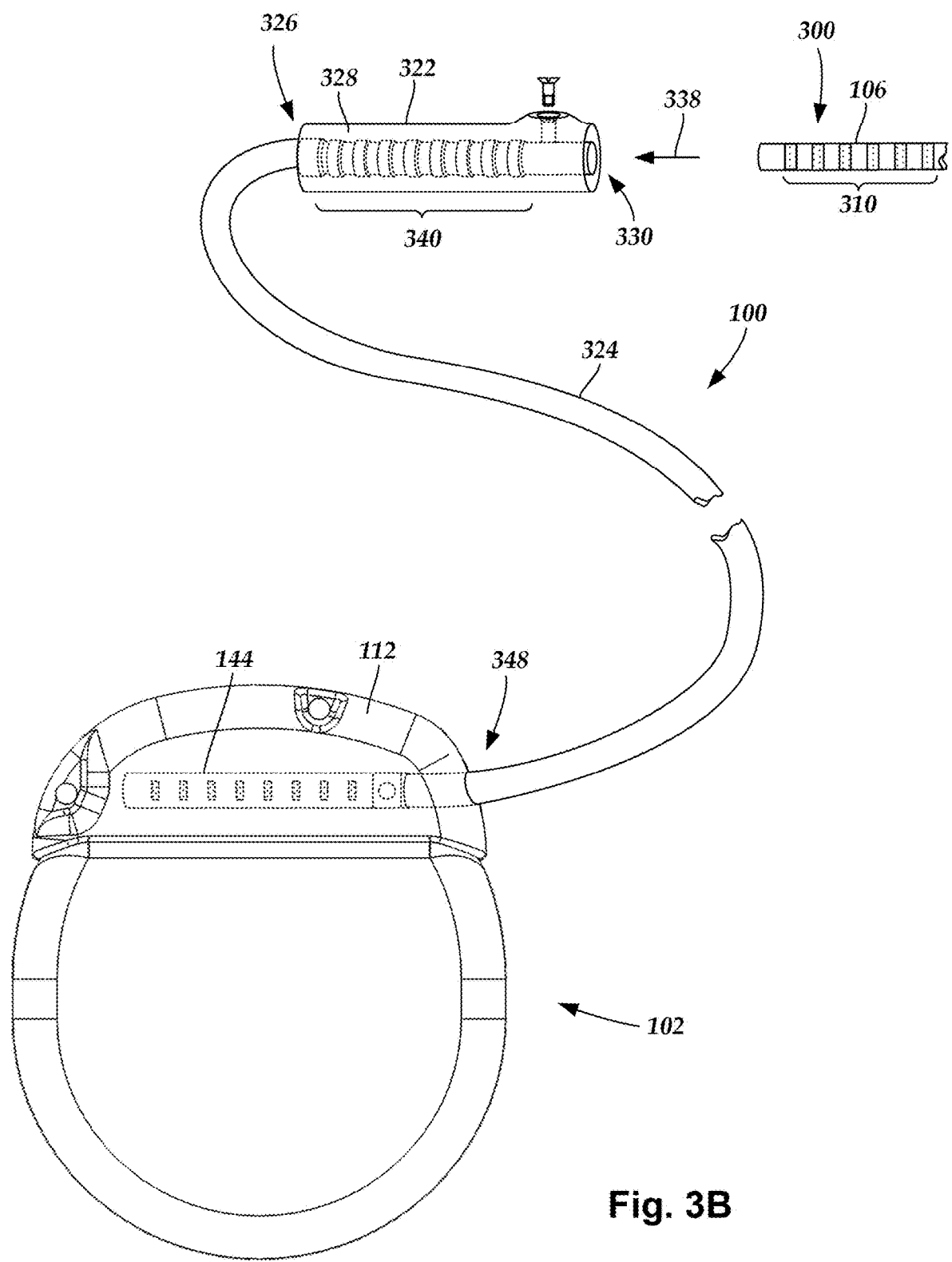
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

The following embodiments of the present invention describe a paddle-style lead, a helical lead, or some combination of both. One or both of the leads can be used for any type of electrostimulation (e.g., neurostimulation, neuromodulation or some other type of electrostimulation). For example, the lead can be used for stimulation of a target tissue such as a target nerve or target organ, and more specifically such as peripheral targets that may include, but are not limited to, peripheral nerves, the sympathetic chain/trunk, the adrenal gland, and other nerves or stimulation targets that may be rather close to a surface of a patient's skin. In at least some embodiments, one or both leads may be implanted in unconstrained environments, so the embodiments described herein provide structures and methods to secure or anchor the leads to the patient's tissue in a vicinity of the target tissue. The paddle-style lead employs active or positive tissue-engagement elements or devices while the helical lead employs a shape and implantation method that permits the helical lead to be wrapped or coiled around the target. In at least some embodiments, the tissue-engagement elements or devices provide for dimensional stability along a longitudinal axis and a lateral axis of the paddle-style lead. The following embodiments may be combined with any of the aspects or features of the aforementioned embodiments.

FIG. 4A is a schematic, perspective view of a paddle-style lead 400 and FIG. 4B is a top, plan view of the paddle-style lead 400. In at least some embodiments, the paddle-style lead 400 includes a paddle body 402, a plurality of electrodes 404 disposed along and within the paddle body 402, and at least one lead body 406 extending from the paddle body 402. In the illustrated embodiment, the paddle body 402 includes a plurality of protuberances 408 extending laterally from the paddle body 402 (but, see FIG. 5 and the respective description thereof for protuberances extending from different portions of the paddle body). The protuberances 408 take the form of a half-circle, but may take a variety of other shapes having a variety of contours such as, but not limited to, beveled edges or rounded edges.

As described above with respect to FIG. 1, any suitable number of electrodes 404 can be disposed on the paddle-style lead including, for example, four, five, six, seven, eight, nine, ten, eleven, twelve, fourteen, sixteen, twenty-four, thirty-two, or more electrodes 404. In FIGS. 4A and 4B, the electrodes 404 are arranged into two columns, where each column has five electrodes 404. In at least some embodiments, the electrodes 404 can be disposed within or mechanically coupled to the paddle body 402 using, for example, an overmolding process, a mechanical bonding process, or a chemical bonding process. When chemically bonded, a primer layer may be applied to the electrodes 404 before any molding or bonding.

The electrodes 404 can be made from any conductive, biocompatible material. Examples of suitable materials include metals, alloys, conductive polymers, conductive carbon, and the like, as well as combinations thereof. In at least some embodiments, one or more of the electrodes 404 are formed from one or more of: platinum, platinum iridium, palladium, palladium rhodium, titanium, stainless steel, or any other suitable biocompatible conductive material (e.g., a conductive polymer). Additionally or alternatively, the electrodes 404 may be coated with a second conductive material that exhibits preferred chemical, electrochemical, or physical properties such as, but not limited to, iridium, iridium oxide, or titanium nitride.

The paddle body 402 can be made from a non-conductive, biocompatible material such as, for example, silicone, polyurethanes (PU), polyetheretherketone ("PEEK"), polytetrafluoroethylene (PTFE), ethylene tetrafluoroethylene (ETFE), polyisobutylene polyurethane (PIB-PUR), poly (styrene-block-isobutylene-block-styrene) (SIBS), epoxy, any other suitable biocompatible material, and any combinations thereof. Additionally or alternatively and with respect to the paddle body 402, the lead body 406, the protuberances 408, or both may be made from similar materials, a similar combination or a different material or materials as the paddle body 402.

FIG. 4C shows a side, elevational view of the paddle-style lead 400 of FIGS. 4A and 4B. In the illustrated embodiment, the paddle body 402 takes the form or a flat or planar paddle-style body (but, see FIGS. 6A-6C and the respective description thereof for a curved-type paddle body). In the case of paddle-style leads, the electrodes 404 can be disposed on the paddle body 402 in any suitable arrangement. The paddle body 402 includes a first surface 410 and an opposing surface 412. The electrodes 404 are flush with one of the surfaces 410 or 412. In the illustrated embodiment, the electrodes 404 are flush with the opposing surface 412.

The paddle-style lead 400 further includes one or more anchoring devices 414. Each anchoring device includes a head element 416 coupled to a tissue-engagement element 418. In the illustrated embodiment, the anchoring device 414 extends through both the paddle body 402 and the protuberance 408. In other embodiments, the anchoring device 414 may extend only through the paddle body 402 or may extend only through the protuberance 408. The head element 416 may take the form of a fastener head having a recess portion, described in more detail with respect to FIG. 6B, configured to receive or engage with a tool. The tissue-engagement element 418 may take the form of an active or positive helical member. The terms "active" and "positive" generally mean that the tissue-engagement elements 418 are urged into the patient's tissue as contrasted with a passive anchoring system such as, for example, holes extending through the paddle body that permit the ingrowth of tissue over time to reduce or prevent undesired lead migration.

In at least some embodiments, the head element 416 and the tissue-engagement element 418 are made from stainless steel. However, these elements 416, 418 can be made from a different material such as materials used for the electrodes or other materials such as MP35N, titanium, rigid plastics or the like. Additionally or alternatively, the head element 416 can made from a different material than the tissue-engagement element 418 or vice-versa.

In at least some embodiments, the paddle-style lead 400 includes two or more tissue-engagement elements 418 that are each contained within the paddle body 402 prior to implantation. The two or more tissue-engagement elements may be configured such that they are not able to fully disengage from the paddle (e.g., not able to back out completely), such that it is not possible for the engagement element to become "lost" in a patient.

Additionally or alternatively, the head element may be protected with a plug or septum, such as a slit polymer plug or a silicone seal plug, that keeps tissue from growing in and around the head element. The plug may be similar to the plugs that are used in many pulse generator headers around set screws that engage a lead terminal.

The illustrated embodiment of FIGS. 4A-4C has four tissue-engagement elements. Once the paddle-style lead 400 is positioned in a selected location within the patient during implantation, then a tool (not shown) is used to engage the head element 416 and rotate the head element 416 until the tissue-engagement element 418 has been extended out of the paddle body 402 and into the patient's tissue by an amount that may be determined during, or prior to, implantation and may differ between patients, situations or because of other factors. In at least some embodiments, the tissue-engagement elements 418 extend from the surface of the paddle body 402 that is flush with the electrodes, which would be the opposing surface 412 in the illustrated embodiment. The tissue-engagement elements 418 may have different configurations depending on the type of tissue to be engaged. In the illustrated embodiment, the tissue-engagement elements 418 are configured with a helical configuration for insertion into the fascia of underlying muscle, into the peritoneum, or into other connective tissue within a vicinity of a target such as a peripheral target. In at least some embodiments, the paddle-style lead 400 can be delivered into the patient through a laparoscopic procedure or through open access procedure. In at least some embodiments, the paddle body 402 may include any number or anchoring devices 414, but preferably at least two anchoring devices. Additionally or alternatively, the anchoring devices can be arranged relative to the paddle body in a variety of ways, for example such as the illustrated embodiment in which the anchoring devices 414 are located adjacent to side portions of the paddle body 402.

Figure 5:
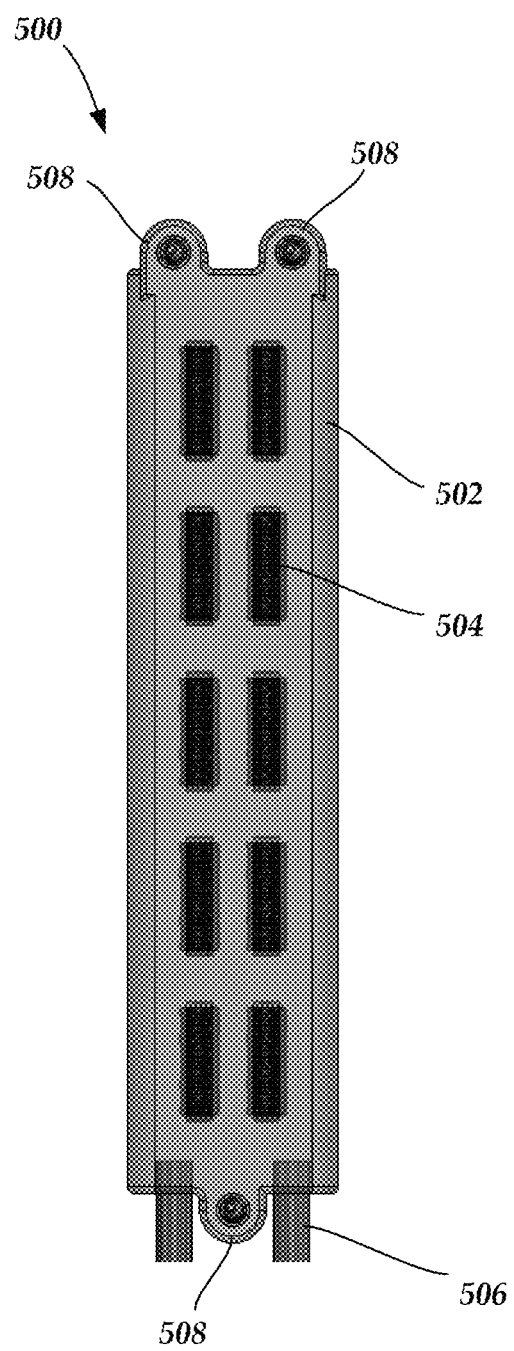
FIG. 5 is a schematic, plan view of another paddle-style lead having a plurality of anchoring devices according to another embodiment of the present invention.

FIG. 5 shows a top, plan view of a paddle-style lead 500. In at least some embodiments, the paddle-style lead 500 includes a paddle body 502, a plurality of electrodes 504 disposed along and within the paddle body 502, and at least one lead body 506 extending from the paddle body 502. In the illustrated embodiment, the paddle body 502 includes a plurality of protuberances 508 extending from end portions of the paddle body 502, as contrasted to extending laterally as shown in FIG. 4B. Again, the protuberances 508 can have the shape or configuration of a half-circle, but may take a variety of other shapes having a variety of contours such as, but not limited to, beveled edges or rounded edges. The protuberances 508 can be integrally formed with the paddle body 502 or mechanically coupled to the paddle body 502. In at least some embodiments, the paddle body 402 may include any number or protuberances 508, but preferably at least two protuberances. Additionally or alternatively, the protuberances can be arranged relative to the paddle body in a variety of ways, for example such as the illustrated embodiment in which the protuberances 508 are located adjacent to end portions of the paddle body 502.

Figure 6A:
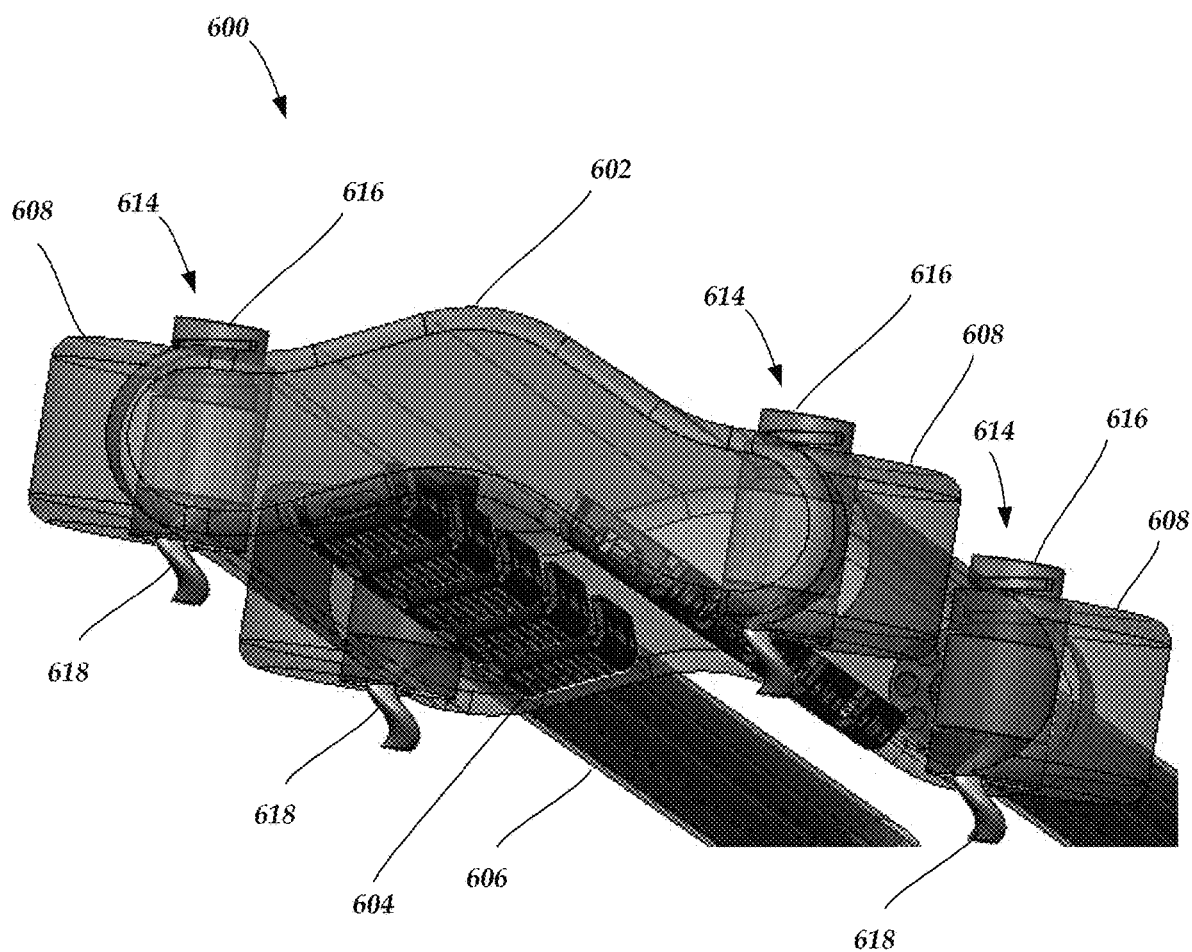
FIG. 6A is a schematic, perspective view of a curved paddle-style lead having a plurality of anchoring devices according to an embodiment of the present invention.
Figure 6B:
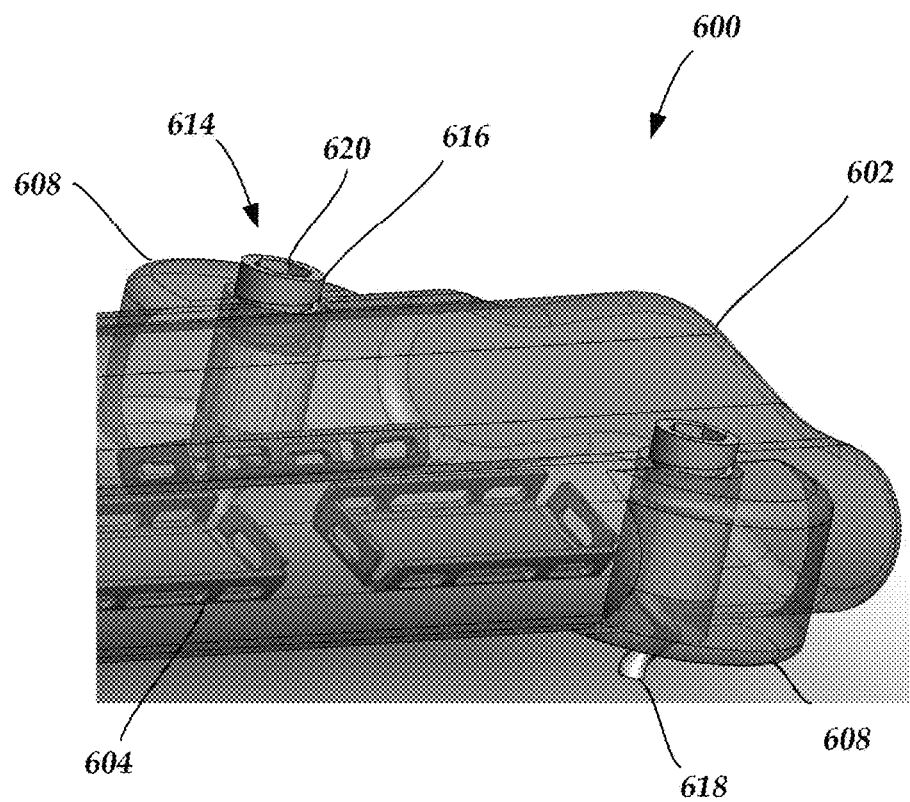
FIG. 6B is a close-up view of at least one of the anchoring devices of the curved paddle-style lead of FIG. 6A.
Figure 6C:
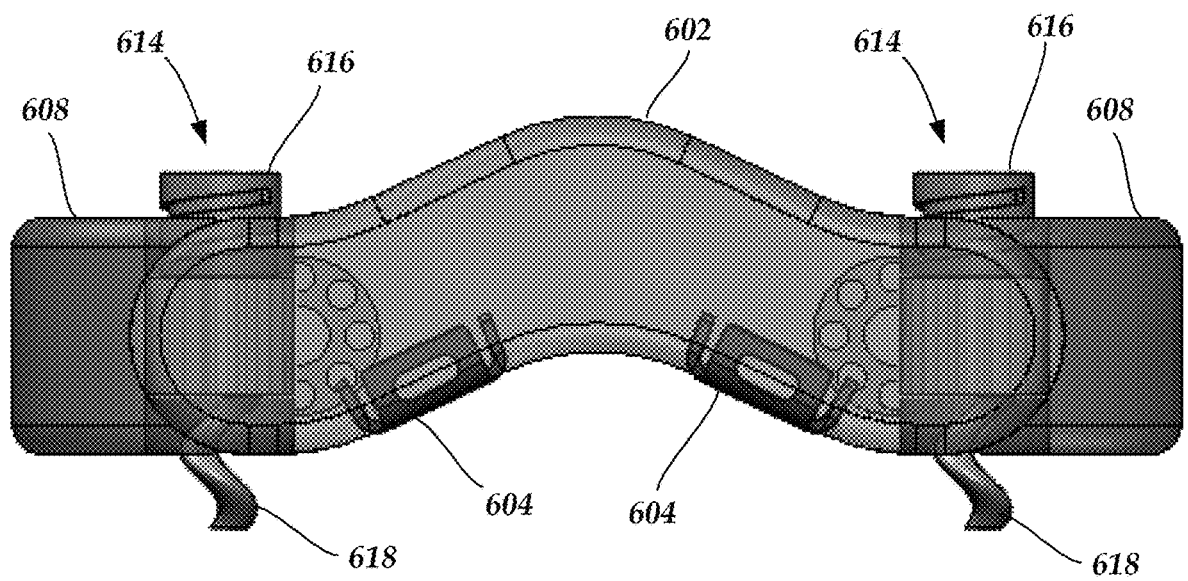
FIG. 6C is an end view of the curved paddle-style lead of FIG. 6A.

FIG. 6A shows a schematic, perspective view of a paddle-style lead 600 having a curved paddle body 602. FIG. 6B shows a close-up view of one of the anchoring devices of the paddle-style lead 600. And, FIG. 6C shows an end view of the paddle-style lead 600 with the anchoring devices actuated or at least partially actuated. In at least some embodiments, a plurality of electrodes 604 are disposed within the curved paddle body 602 and flush with a concave surface of the curved paddle body 602. Similar to the paddle-style lead 400 described above, the paddle-style lead 600 includes protuberances 608 that are arranged relative to the curved paddle body 602. In at least some embodiments, the curved section of the paddle body 602 is located between the anchoring devices, protuberances or both. Additionally or alternatively, the curved section is configured for placement over a target such as, but not limited to, a peripheral nerve.

In at least some embodiments, the curved paddle body 602 may be tailored for a specific tissue, nerve or organ size, or in some cases, be tailored to be patient-specific to match an anatomy size found during pre-operative imaging. While the illustrated, curved paddle body 602 is shown to be curved about the long axis, it is appreciated that the curved paddle body may also be curved about the short axis (e.g., to curve around an organ).

Referring to FIG. 6B, the paddle-style lead 600 includes anchoring devices 614 each having a head element 616 coupled to a tissue-engagement element 618. In the illustrated embodiment, each anchoring device 614 extends through both the curved paddle body 602 one of the respective protuberances 608. In at least some other embodiments, the anchoring device 614 may extend only through the paddle body 602 or may extend only through the protuberance 608.

The head element 616 may take the form of a socket head or hex socket having a recessed portion 620 configured to receive or engage with a tool (not shown). In the illustrated embodiment, the head element comprises a recessed portion 620 having a hexagonal configuration for receiving tool, which may take the form of a hex key, hex wrench or Allen wrench. In at least some other embodiments, the head element 616 may have a different configuration for engagement with a different type of torque-application tool. By way of example, the head element may take the form of a flathead, Philips, square, or star-shape pattern.

Referring to FIG. 6C, the tissue-engagement element 618 is a spiraling, helical rod threadably coupled to the head element 616. The helical rod may vary in diameter, pitch and pitch angle over a length of the helical rod. Additionally or alternatively, each anchor device 614 of a single paddle-style lead 600 may each have its own configuration depending on the local tissue to be engaged. In other embodiments, the tissue-engagement element may be an externally threaded rod that extends from the paddle body. In yet other embodiments, a single anchoring device 614 may include more than one tissue-engagement element 618.

Figure 7:
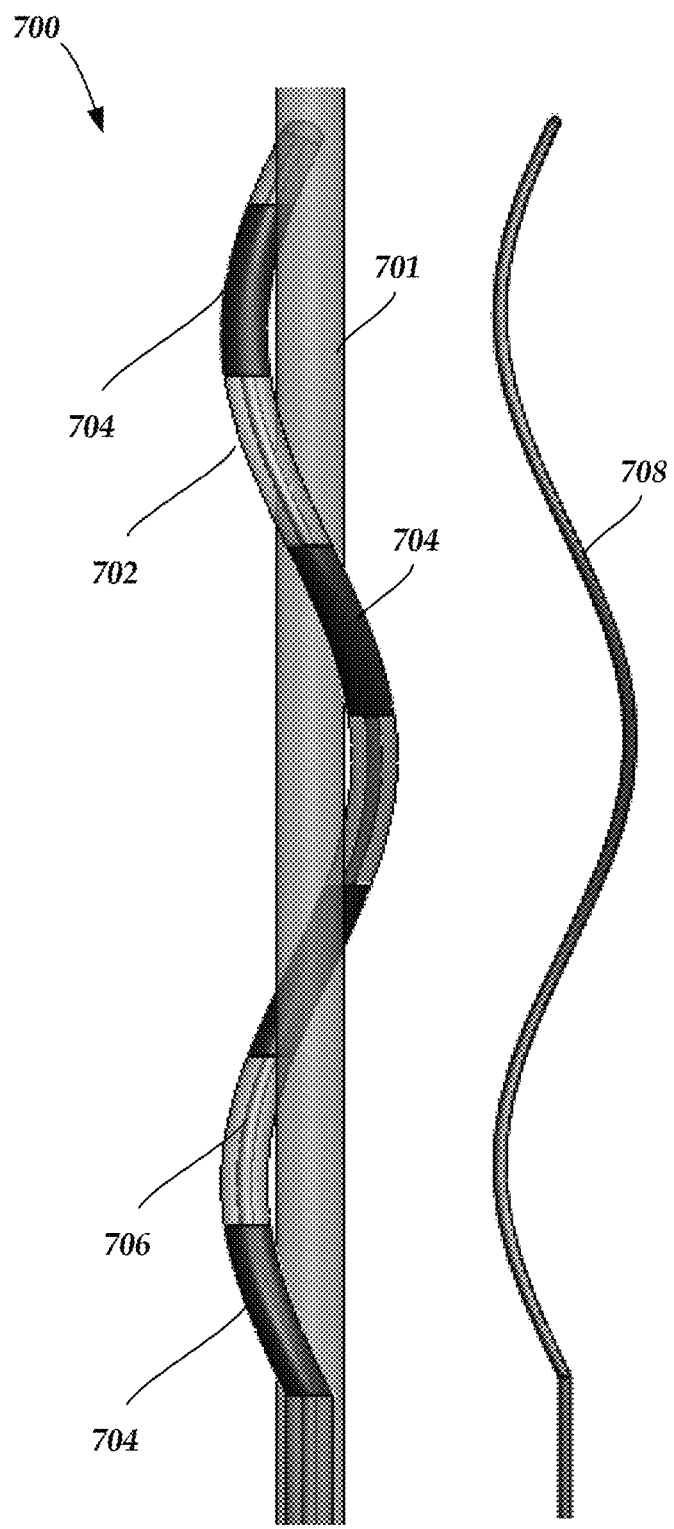
FIG. 7 is a schematic, perspective view of a helical lead according to an embodiment of the present invention.

FIG. 7 is a schematic, plan, exploded view of a distal end portion of a helical lead 700 for electrostimulation of a target tissue 701, which according to at least some embodiments may take the form of a peripheral nerve. In at least some embodiments, the helical lead 700 includes a lead body 702, a plurality of electrodes 704 (e.g., circumferential or segmented electrodes), and a lumen 706 configured to receive a guidewire or stylet 708. The helical lead 700 operates to wrap around the target tissue 701 to reduce lead migration and to provide more effective electrostimulation of the target tissue 701.

In at least some embodiments, inserting the stylet 708 causes the distal end portion of the lead 700 to have a helical shape. It will be understood that the lead can be bent into other shapes using the stylet 708. In at least some embodiments, the stylet 708 is inserted through the lumen 706 that extends along at least a portion of the lead including, preferably, the distal end portion of the lead 700. It will also be understood that more than one guidewire or stylet can be used and may be inserted into the same lumen or different lumens within the lead. In at least some embodiment, the stylet 708 may have an amount of stiffness that allows it to be delivered along the target tissue 701 by rotating the lead 700 with the stylet 708 inserted such that the lead 700 is forced to "corkscrew" around the target tissue 701. In at least some embodiments, the stylet 708 is made from nitinol, but it is appreciated that other materials may be used for the stylet.

In at least some embodiments, the lead body 702 may be molded to have a loose helical shape before insertion or retraction of the stylet 708 while the stylet 708 is straight when inserted into the lumen 706. Insertion of the stylet 708 causes the lead 700 to straighten and removal of the stylet 708 causes the lead 700 to take on the helical shape or twist. In at least some other embodiments, the stylet 708 has a helical shape and causes a straight lead to take on the helical shape before insertion into or after retraction of the stylet 708 from the lumen 706.

In at least some embodiments, the stylet 708 may remain in the lead 700 after implantation to retain the helical or other shape of the distal end of the lead 700. In other embodiments, the stylet 708 may be removed after implantation and the distal end of the lead 700 is arranged to maintain the helical or other shape on its own.

Figure 8A:
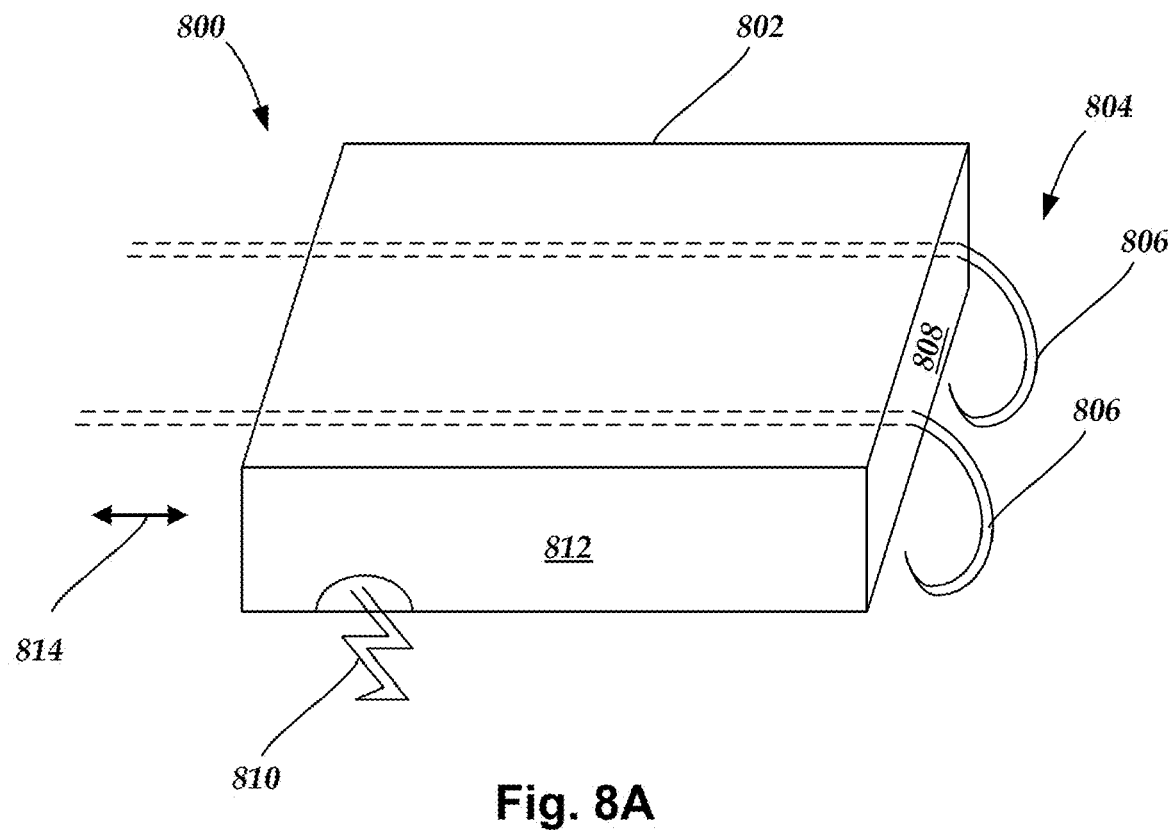
FIG. 8A is a schematic, perspective view of a paddle-style lead having deployable and retractable tissue-engagement devices according to an embodiment of the present invention.
Figure 8B:
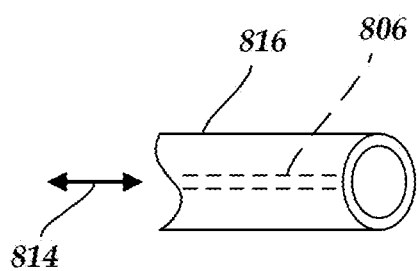
FIG. 8B is a close-up view of a tissue-engagement device retracted in a lumen according to an embodiment of the present invention.
Figure 8C:
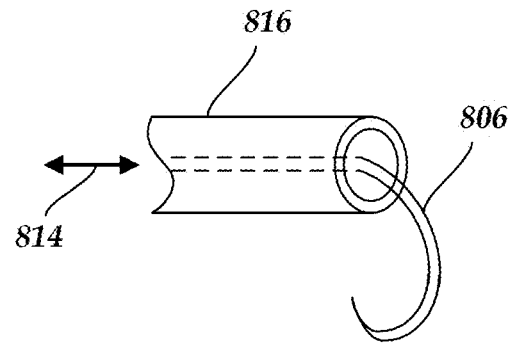
FIG. 8C is a close-up view of the tissue-engagement device of FIG. 8B extending from the lumen according to an embodiment of the present invention.

FIG. 8A shows a schematic view of a paddle-style lead 800 having a paddle body 802 and a manipulatable paddle fixation system 804. FIGS. 8B and 8C show schematic, close-up views of the paddle fixation system 804 during deployment. In at least some embodiments, one or more tissue-engagement devices may be deployed from the paddle body 802 at various locations, for example from any of the distal, proximal, lateral, top and bottom surfaces of the paddle body 802. In the illustrated embodiment, first tissue-engagement devices 806 extend from the distal surface 808 of the paddle body 802 and a second tissue-engagement device 810 extends from a lateral surface 812 of the paddle body 802. In at least some embodiments, the first tissue-engagement devices 806 have a hooked or curved shape while the second tissue-engagement device 810 has a spiral, coiled or helical shape, however it is understood that the tissue-engagement devices 806, 810 may take a variety of shapes. In at least some embodiments, the tissue-engagement devices 806, 810 are made from a shape memory material such as, but not limited to, nitinol.

In at least some embodiments, deployment or retraction of the tissue-engagement devices 806, 810 may be accomplished by using a tool, such as forceps, to translate or otherwise urge the tissue-engagement devices 806, 810 out of or back into the paddle body 802 as indicated by arrow 814. In other embodiments, a mechanism (not shown) coupled to a proximal end of the lead 800 may be used to deploy or retract the tissue-engagement devices 806, 810. The mechanism may be manipulated, rotated or otherwise actuated to cause the tissue-engagement devices 806, 810 to deploy or retract from the paddle body 802.

FIG. 8B shows a close-up view of the tissue-engagement device 806 in a retracted position within a lumen 816. FIG. 8C shows a close-up view of the tissue-engagement device 806 in a deployed position relative to the lumen 816. In at least some embodiments, the lumen 816 extends through the paddle body 802.

Figure 9A:
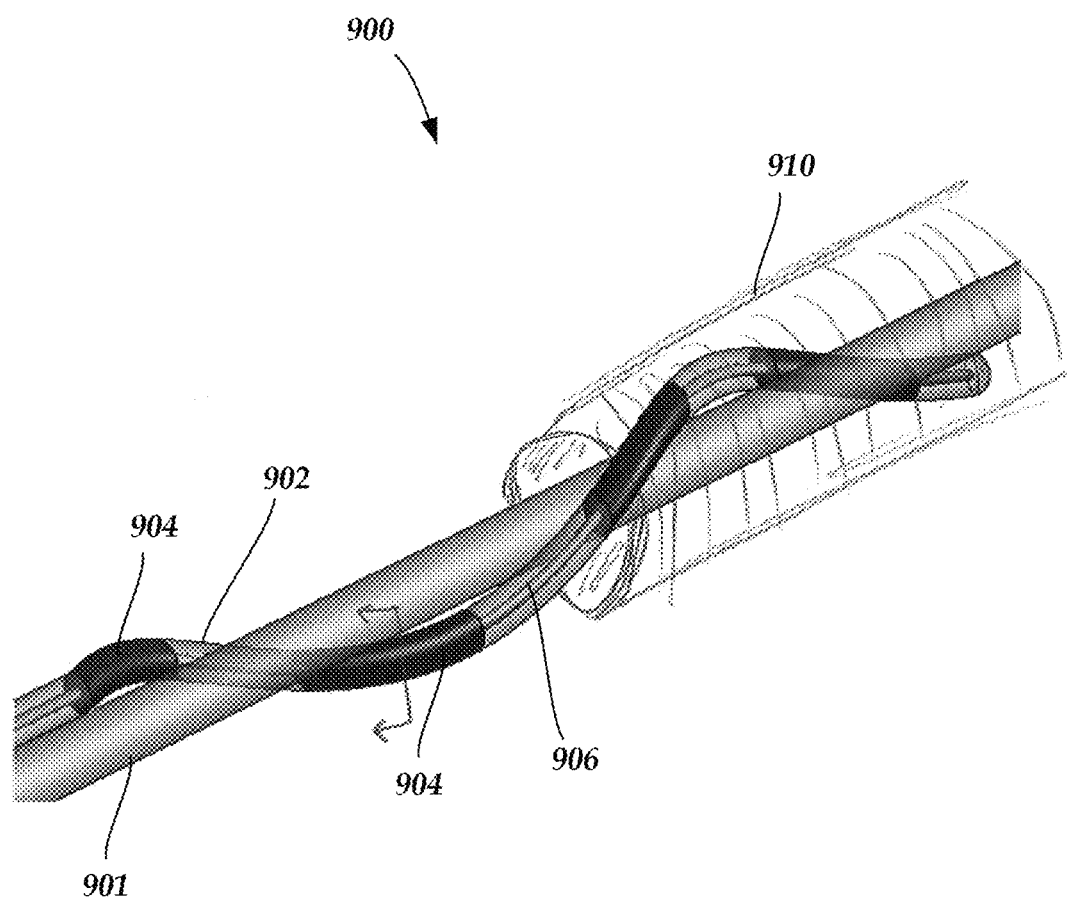
FIG. 9A is a schematic, perspective view of a sheath covering at least a portion of a helical lead according to an embodiment of the present invention.

FIG. 9A shows a schematic, perspective view of a helical lead 900 wound around and along a target tissue 901 and covered, at least partially, by a sheath 910. Similar to FIG. 7, the helical lead 900 includes a lead body 902, a plurality of electrodes 904 (e.g., circumferential or segmented electrodes), and a lumen 906 configured to receive a guidewire or stylet (not shown). In at least some embodiments, the sheath 910 functions as an insulator to reduce or prevent electrostimulation of surrounding tissue. Accordingly, the sheath 910 is made from an insulating material.

FIGS. 9B-9D show schematic, perspective views of several different types of sheaths according to various embodiments of the invention. FIG. 9B shows a sheath 910*a* having a longitudinal slit 912*a* that permits the sheath to be laterally slid or placed over the lead (e.g., generally referred to as "side loading"). FIG. 9C shows a sheath 910*b* having a spiral or helical shaped slit 912*b* that permits the sheath to be wrapped around the lead in a corkscrew or twisting manner. FIG. 9D shows a sheath 910*c* having a longitudinal slit 912*c* that allows the lead to be received into a first channel 914*c*. After the lead is positioned vis-à-vis the target tissue, the lead can be urged into a second channel 916*c*, which is smaller than the first channel 914*c* and configured to engage with and retain the lead within the second channel 916*c*.

Figure 10:
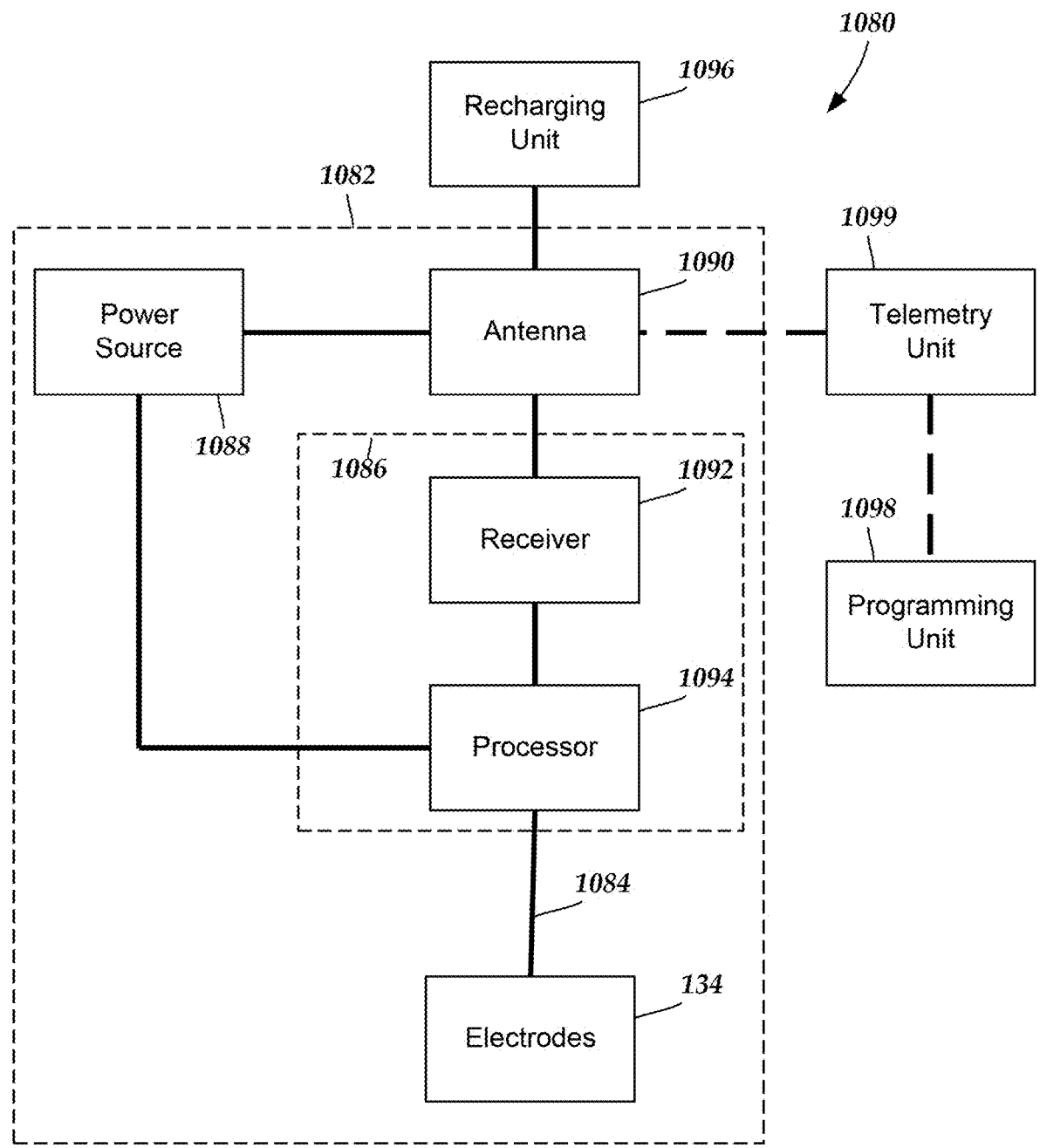
FIG. 10 is a schematic diagram of an electrical stimulation system according to an embodiment of the present invention.

FIG. 10 is a schematic overview of one embodiment of components of an electrical stimulation arrangement 1080 that includes an electrical stimulation system 1082 with a lead 1084, stimulation circuitry 1086, a power source 1088, and an antenna 1090. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 1088 is a rechargeable battery or chargeable capacitor, the power source may be recharged/charged using the antenna 1090, if desired. Power can be provided for recharging/charging by inductively coupling the power source 1088 through the antenna 1090 to a recharging unit 1096 external to the user. Examples of such arrangements can be found in the references identified above.

In one embodiment, electrical current is emitted by the electrodes (such as electrodes 134 in FIG. 1) on the lead 1084 to stimulate nerve fibers, muscle fibers, or other body tissues near the electrical stimulation system. The stimulation circuitry 1086 can include, among other components, a processor 1094 and a receiver 1092. The processor 1094 is generally included to control the timing and electrical characteristics of the electrical stimulation system. For example, the processor 1094 can, if desired, control one or more of the timing, frequency, strength, duration, and waveform of the pulses. In addition, the processor 1094 can select which electrodes can be used to provide stimulation, if desired. In some embodiments, the processor 1094 selects which electrode(s) are cathodes and which electrode(s) are anodes. In some embodiments, the processor 1094 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1098 that, for example, allows modification of pulse characteristics. In the illustrated embodiment, the processor 1094 is coupled to a receiver 1092 which, in turn, is coupled to the antenna 1090. This allows the processor 1094 to receive instructions from an external source to, for example, direct the pulse characteristics and the selection of electrodes, if desired.

In one embodiment, the antenna 1090 is capable of receiving signals (e.g., RF signals) from an external telemetry unit 1099 that is programmed by the programming unit 1098. The programming unit 1098 can be external to, or part of, the telemetry unit 1099. The telemetry unit 1099 can be a device that is worn on the skin of the user or can be carried by the user and can have a form similar to a pager, cellular phone, or remote control, if desired. As another alternative, the telemetry unit 1099 may not be worn or carried by the user but may only be available at a home station or at a clinician's office. The programming unit 1098 can be any unit that can provide information to the telemetry unit 1099 for transmission to the electrical stimulation system 1082. The programming unit 1098 can be part of the telemetry unit 1099 or can provide signals or information to the telemetry unit 1099 via a wireless or wired connection. One example of a suitable programming unit is a computer operated by the user or clinician to send signals to the telemetry unit 1099.

The signals sent to the processor 1094 via the antenna 1090 and the receiver 1092 can be used to modify or otherwise direct the operation of the electrical stimulation system 1082. For example, the signals may be used to modify the pulses of the electrical stimulation system such as modifying one or more of pulse duration, pulse frequency, pulse waveform, and pulse strength. The signals may also direct the electrical stimulation system 1082 to cease operation, to start operation, to start charging the battery, or to stop charging the battery.

Optionally, the electrical stimulation system 1082 may include a transmitter (not shown) coupled to the processor 1094 and the antenna 1090 for transmitting signals back to the telemetry unit 1099 or another unit capable of receiving the signals. For example, the electrical stimulation system 1082 may transmit signals indicating whether the electrical stimulation system 1082 is operating properly or not or indicating when the battery needs to be charged or the level of charge remaining in the battery. The processor 1094 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
   at least one lead body having a distal end portion, a proximal end portion, and a longitudinal length;
   a paddle body extending from the distal end portion of the at least one lead body;
   a plurality of electrodes disposed along the paddle body;
   a plurality of terminals disposed along the proximal end portion of the at least one lead body;
   a plurality of conductors electrically coupling the plurality of terminals to the plurality of electrodes; and
   an anchoring device threadably disposed in at least a portion of the paddle body, the anchoring device having a head element and a tissue-engagement element fixed to the head element,
   wherein rotation of the head element in a first direction urges the tissue-engagement element to extend out of the paddle body and rotation of the head element in a second direction, opposite the first direction, urges the tissue-engagement element to retract into the paddle body.

2. The lead of claim 1, wherein the paddle body includes a protuberance extending from a remainder of the paddle body, wherein at least a portion of the anchoring device is disposed in the protuberance.

3. The lead of claim 1, wherein the head element includes a recessed region configured to be engaged by a tool.

4. The lead of claim 3, wherein the recessed region is hexagonally shaped.

5. The lead of claim 1, further comprising at least one additional anchoring device threadably disposed in a different portion of the paddle body.

6. The lead of claim 1, wherein the tissue-engagement element is a helical member.

7. The lead of claim 1, wherein the anchoring device is disposed along a side portion of the paddle body.

8. The lead of claim 1, wherein the anchoring device is disposed along an end portion of the paddle body.

9. The lead of claim 1, wherein the paddle body includes a curved section located between the anchoring device and at least one additional anchoring devices, the curved section configured for placement over a target tissue.

10. The lead of claim 1, further comprising a plug or septum disposed over the head element of the anchoring device.

11. The lead of claim 1, wherein the tissue-engagement element is configured so that the tissue-engagement element cannot fully disengage from the paddle body.

12. The lead of claim 1, wherein the tissue-engagement element is a spiraling, helical rod.

13. An electrical stimulation system comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end portion of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed on the proximal end portion of the lead body of the electrical stimulation lead.

14. The electrical stimulation system of claim 13, further comprising a lead extension coupleable to both the electrical stimulation lead and the control module.

15. An arrangement for electrical stimulation of a target tissue, the arrangement comprising:
an electrical stimulation lead comprising
a lead body having a distal end portion, a proximal end portion, and a longitudinal length,
a plurality of electrodes disposed along the distal end portion of the lead body,
a plurality of terminals disposed along the proximal end portion of the lead body, and
a plurality of conductors electrically coupling the plurality of terminals to the plurality of electrodes; and
a stylet configured for insertion into the lead body, wherein the stylet is helically shaped;
wherein, when the stylet is inserted into the lead body and the lead is implanted in the target tissue, at least the distal end portion of the lead body forms a helical shape that variably locates the plurality of electrodes around the target tissue in both a longitudinal and circumferential direction.

16. The lead of claim 15, wherein the stylet is nitinol wire.

17. A method of implanting an electrical stimulation lead, the method comprising:
moving a distal end portion of the lead of the arrangement of claim 15 to be within a vicinity of a target tissue;
from a proximal end portion of the lead, inserting the stylet longitudinally into the lead; and
manipulating the stylet to urge the distal end portion of the lead body of the lead to helically wrap around the target tissue.

18. The method of claim 17, wherein inserting the stylet includes inserting a nitinol guidewire.

19. An electrical stimulation lead for stimulating a target tissue, the lead comprising:
a lead body having a distal end portion, a proximal end portion, and a longitudinal length;
a plurality of electrodes disposed along the distal end portion of the lead body;
a plurality of terminals disposed along the proximal end portion of the lead body;
a plurality of conductors electrically coupling the plurality of terminals to the plurality of electrodes;
a sheath configured for locating over at least a section of the distal end portion of the lead body, wherein the sheath includes a slit for sliding the sheath over the lead body and the target tissue,
wherein at least the distal end portion of the lead body includes a helical shape that, when implanted in the target tissue, variably locates the plurality of electrodes around the target tissue in both a longitudinal and circumferential direction.

20. The lead of claim 19, wherein the distal end portion of the lead body is molded into the helical shape.

* * * * *